United States Patent [19]

Kousai et al.

[11] Patent Number: 4,874,374
[45] Date of Patent: Oct. 17, 1989

[54] MEDICAL TOOL INTRODUCTION CANNULA AND METHOD OF MANUFACTURING THE SAME

[75] Inventors: Tadashi Kousai; Toshinobu Ishida; Yousuke Moriuchi, all of Fuji, Japan

[73] Assignee: Terumo Kabushiki Kaisha, Tokyo, Japan

[21] Appl. No.: 329,799

[22] Filed: Mar. 28, 1989

Related U.S. Application Data

[62] Division of Ser. No. 176,601, Apr. 1, 1988.

[30] Foreign Application Priority Data

Apr. 8, 1987 [JP] Japan ................................. 62-86251
Aug. 14, 1987 [JP] Japan ............................... 62-202858

[51] Int. Cl.⁴ .......................................... A61M 25/00
[52] U.S. Cl. ..................................... 604/164; 604/280
[58] Field of Search ............................. 604/164–170, 604/280–284

[56] References Cited

U.S. PATENT DOCUMENTS

| | | | |
|---|---|---|---|
| 3,119,392 | 1/1964 | Zeiss | 128/328 |
| 3,616,990 | 11/1971 | Powell | 229/66 |
| 4,402,685 | 9/1983 | Buhler et al. | 604/280 |
| 4,747,833 | 5/1988 | Kousai | 604/164 |
| 4,776,846 | 10/1988 | Wells | 604/161 |
| 4,781,690 | 11/1988 | Ishida et al. | 604/164 |

*Primary Examiner*—Dalton L. Truluck
*Attorney, Agent, or Firm*—Frishauf, Holtz, Goodman & Woodward

[57] ABSTRACT

Medical instrument introduction cannula, which is useful as a guide means for introducing and indwelling a rod-like medical instrument such as a catheter and a guide wire. This cannula is removed after use from the medical instrument by being splitted. This cannula is formed of a hollow tubular body having a strip member consisting of a material different from the other portion of the tubular body, which extends over the entire or almost the entire length of the tubular body. The strip member has a weld line along the length of the strip member, or consists of a resin which exhibits a good bonding property only to one of the other components forming the tubular body. The tubular body can be splitted by way of the weld line or the removal of the strip member having such a bonding property. The method of manufacturing the medical instrument introduction cannular by a two-color extruder is also disclosed.

7 Claims, 5 Drawing Sheets

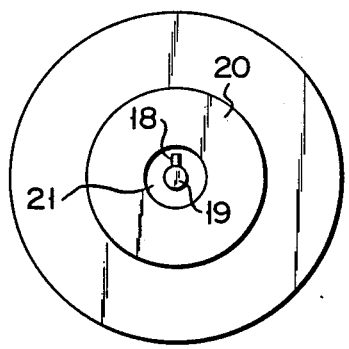
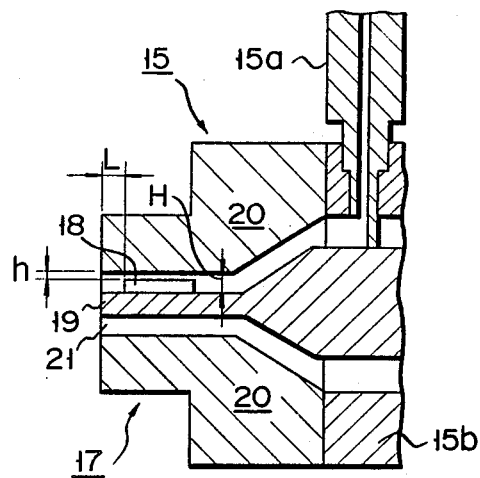
FIG. 4  FIG. 5
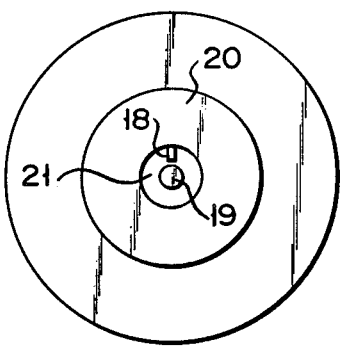
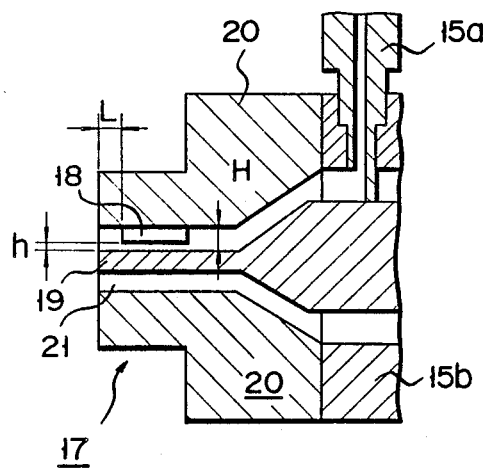
FIG. 6  FIG. 7

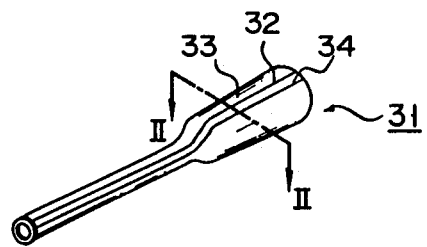 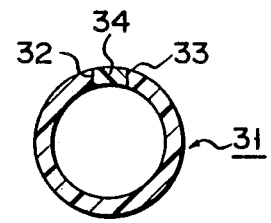
FIG. 11　　　　　FIG. 12
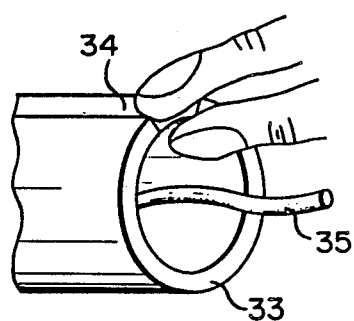 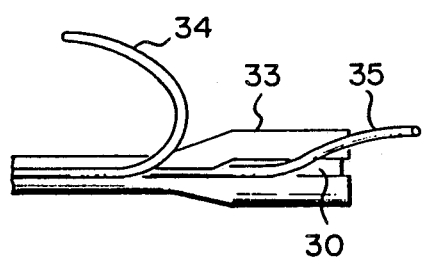
FIG. 13　　　　　FIG. 14

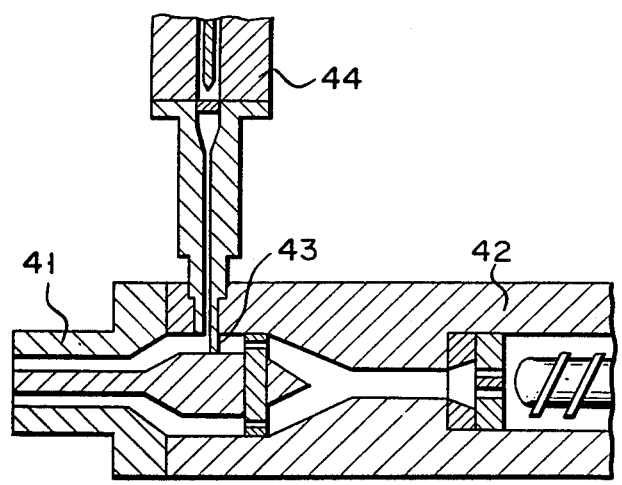
F I G. 15
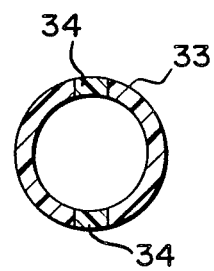
F I G. 16

MEDICAL TOOL INTRODUCTION CANNULA AND METHOD OF MANUFACTURING THE SAME

This is a division of application Ser. No. 07/176,601 filed Apr. 1, 1988, pending.

BACKGROUND OF THE INVENTION

1. Title of the Invention

The present invention relates to a synthetic resin introduction cannula used for introducing and indwelling a rod-like medical tool such as a catheter, a guide wire, or the like in a blood vessel, and a method of manufacturing the same.

2. Description of the Related Art

Conventionally, when a catheter is introduced and indwelled in a blood vessel, a flexible introduction cannula of a synthetic resin is used. More specifically, an introduction cannula is fitted on an inner cannula of a syringe so that the distal end of the inner cannula projects therefrom. The inner cannula is then pierced into a blood vessel until the distal end of the introduction cannula is inserted in the blood vessel. Then, the inner cannula is removed from the blood vessel while the introduction cannula is left in position. In this manner, a desired catheter is inserted in the introduction cannula while the introduction cannula is left in the blood vessel, and the distal end portion of the catheter is then inserted in the blood vessel. After the catheter is indwelled at a predetermined position in the blood vessel, the unnecessary introduction cannula is removed from the blood vessel. Preferably, the introduction cannula is also removed from the catheter. It is undesirable for sanitary reasons that the introduction cannula is left in the body after being removed from the blood vessel. In addition, the introduction cannula in this state disturbs the subsequent operations.

However, it is impossible to pull out the introduction cannula from the catheter since an extended portion such a connector of the catheter is present.

For this reason, some proposals for removing the used introduction cannula from the catheter have been made. For example, in one proposal, a slit is preformed in the longitudinal direction of the introduction cannula, and the introduction cannula is removed from the catheter through the slit.

In Japanese Patent Disclosure (Kokai) No. 56-11069, a pair of linear members of a single plastic material different from that of the remaining portion are formed in opposing portions in the radial direction of an introduction tube. The base portion of an introduction cannula is coupled to a fitting portion with an inner cannula hub with a slit, which is coupled to the linear members. The used introduction cannula is torn at the linear members to be split into two portions while gripping the fitting portion.

However, in the former method, the mechanical strength of the introduction cannula is decreased, resulting in poor operability. In addition, when a cannula is introduced into a blood vessel, blood may leak from the slit. In the latter method, the linear members are easily cracked upon post-machining, e.g., cutting, distal end machining, and the like of the introduction cannula or handling as a product. An introduction cannula with cracked linear members cannot be used, and, if used, blood leakage may occur.

In the introduction cannula having linear members for splitting the introduction cannula as described above, since the color of the strip members resembles that of the introduction cannula body, it is difficult to immediately confirm the positions of the strip members when they are removed from the introduction cannula body, resulting in cumbersome splitting operation of the introduction cannula.

SUMMARY OF THE INVENTION

The present invention has been made in consideration of the above situation and has as its object to provide a medical tool introduction cannula which can be free from inadvertent peeling or splitting upon post-machining or during handling as a product, and can be easily split and removed from a catheter or the like after it is used, and a method of manufacturing the same.

According to the present invention, as a first means for achieving the above object, there is provided a medical tool introduction cannula for introducing a rod-like medical tool in a living body, wherein the introduction cannula comprises a hollow tubular body of a synthetic resin allowing the rod-like medical tool to extend therethrough, a portion of the hollow tubular body is composed of a strip member of a material different from a main portion of the hollow tubular body to extend over the entire length in the longitudinal direction of the tubular body or over the entire length in the longitudinal direction excluding a distal end portion, and a weld line is longitudinally formed in the strip member.

The distal end of the tubular body is preferably tapered thinner to be in tight contact with an inner cannula inserted therethrough, and its base portion is preferably tapered thicker. The main portion of the hollow tubular body is preferably formed of a thermoplastic material, such as polypropylene (PP), highdensiy polyethylene, semi-hard polyvinyl chloride, fluoro plastics, or the like. It is also preferable that the main portion of the hollow tubular body has a some degree of flexibility that is sufficient to allow a catheter to be introduced thereinto, as the hollow tubular body is being inserted in a human body, and to allow the hollow tubular body to be removed from the cather introduced therein. The strip member is preferably formed of a thermoplastic material such as a blend polymer of EVA and PP, a blend polymer of polyethylene and EVA, or the like.

According to the present invention, as another means for solving the above problem, there is provided a method of manufacturing the medical tool introduction cannula, wherein molding resin flows for forming the strip member are divided by at least one buffer plate arranged near a die outlet port of a molding resin flow path of an extruder and are subsequently joined to be extruded from the die outlet port.

The buffer plate is preferably arranged at a position separated from the edge portion of the die outlet port by 0 to 5 mm, and preferably has a height ½ or more of that of the resin flow path of the die. Note that a melted resin flow is once divided in a cylinder, and the divided flows are joined and coupled again. In this specification, the weld line means a portion where fusion bonding of the coupled portion is incomplete, and a mechanical strength is decreased.

According to the present invention, as a second means for achieving the above object, there is provided a medical tool introduction cannula for introducing a rod-like medical tool such as a catheter into a living body, wherein the introduction cannula comprises a tubular body having a longitudinal hollow portion capable of receiving the medical tool therethrough, the tubular body consists of a plurality of strip members which are liquid-tightly integrated to extend along the longitudinal direction of the tubular body, one strip member consists of a molded body of a mixture of a plurality of materials, one of which has no bonding property with at least one material of the other strip member contacting thereto and the other having good bonding property therewith, the strip members are bonded with a strength with which the strip members can be separated by a predetermined force, and after the medical tool is introduced, the strip members are separated by the predetermined force to remove the introduction cannula from the medical tool inserted in the hollow portion.

Furthermore, in the medical tool introduction cannula according to the second means of the present invention, one of the strip members is a molded body of a mixture of first and second materials, the other strip member contacting the one strip member is a molded body of a third material, the first and third materials essentially have no bonding property with each other, and the second and third materials have a good bonding property with each other.

In the introduction cannula according to the second means of the present invention, the first material consists of a polyolefin-based resin such as high-density polyethylene, polypropylene, an ethylene-propylene copolymer, or the like, the second material consists of a material prepared by modifying the polyolefin-based resin with maleic acid to improve the bonding property with the third material, and the third material consists of a polyamide resin such as 6-nylon, 6,6-nylon, 11-nylon, and the like; or a polyester resin such as polyethylene terephthalate, polybutylene terephthalate, or the like.

The first material may have no compatibility with the second material, and the second and third materials may consist of an identical material.

Note that each of the second and third materials may consist of a polymer blend of a plurality of types of polymers.

Furthermore, according to the present invention, in order to achieve the above object, in the medical tool introduction cannula according to the first or second means (or feature), the strip member to be split or peeled is formed to have a color quite different from that of the remaining portion of the hollow tubular body.

The phrase "the strip member is formed to have a color quite different from that of the remaining portion of the hollow tubular body" means that only the strip member or only the remaining portion of the hollow tubular body is colored by a coloring agent or both are colored to have a noticeable color difference.

BRIEF DESCRIPTION OF THE DRAWINGS

FIG. 4 is a front view of a manufacturing apparatus of the medical tool introduction cannula of FIG. 1;

FIG. 5 is a sectional view of the manufacturing apparatus of FIG. 4;

FIG. 6 is a front view of another manufacturing apparatus of the medical tool introduction cannula;

FIG. 7 is a sectional view of the manufacturing apparatus of FIG. 6;

FIG. 11 is a perspective view of a medical tool introduction cannula according to the second features of the present invention;

FIG. 12 is a sectional view taken along the line II—II of FIG. 11;

FIGS. 13 and 14 are perspective view explaining the operation for peeling a strip from the medical tool introduction cannula;

FIG. 15 is a sectional view showing a manufacturing apparatus for producing the medical tool introduction cannula; and FIG. 16 is a sectional view of a medical tool introduction cannula according to another embodiment of the present invention.

DETAILED DESCRIPTION OF THE PREFERRED EMBODIMENTS

Figure 1:
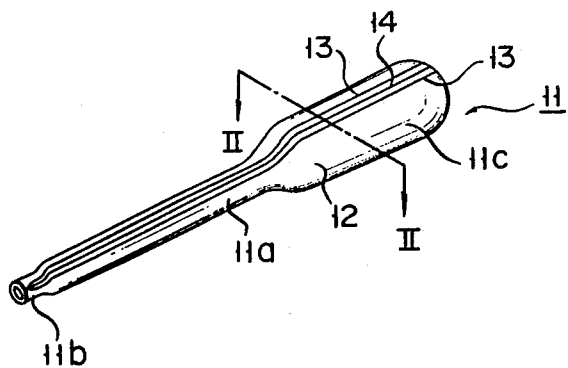
FIG. 1 is a perspective view of the medical tool introduction cannula according to the first feature of the present invention.

The present invention according to the first means will be described with reference to FIGS. 1 to 5. FIG. 1 is a perspective view of medical tool introduction cannula 11 according to the present invention. Introduction cannula 11 comprises a hollow tubular body having two open ends through which a rod-like medical tool such as a catheter can be inserted. Cannula 11 has a cylindrical shape in which central portion 11 has a size of, e.g., 12G to 16G, distal end portion 11b is tapered thinner to be in tight contact with an inner cannula (not shown), and base portion 11c is tapered thicker.

Figure 2:
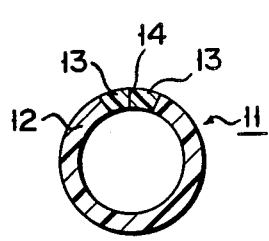
FIG. 2 is a sectional view taken along the line II—II of FIG. 1.

As shown in FIGS. 1 and 2, strip member 13 is formed in a specific portion along the circumferential direction of the tubular body to extend over the entire length in the longitudinal direction of the tubular body. Strip member 13 has physical properties different from main portion 12. Weld line 14 is formed at a substantially intermediate portion in the widthwise direction of strip member 13 to extend in the longitudinal direction. Main portion 12 preferably consists of a relatively hard synthetic resin material in view of operability of introduction cannula 11 as a whole. Examples of the synthetic resin are polypropylene, high-density polyethylene, semi-hard polyvinyl chloride, poly-4-methylpentene-1, and polycarbonate. Strip member 13 can consist of a soft thermoplastic resin material having good compatibility with main portion 12. Examples of the thermoplastic resin include appropriate blend polymers such as a polypropylene/ethylene-vinyl acetate copolymer, a high-density polyethylene/ethylene-vinyl acetate copolymer, polypropylene/polyethylene, a methylpentene polymer/ethylene-vinyl acetate copolymer, methylpentene polymer/polyethylene, and the like. If the main portion and the strip member are formed of materials having extremely different properties in terms of compatibility, they easily crack at their boundary, and post-machining is rendered very difficult. Strip member 13 need not always be formed over the entire length of the tubular body as shown in FIG. 1. For example, strip member 13 may be omitted at the distal end portion to increase the mechanical strength of this portion. In addition, weld line 14 may be omitted in the distal end portion of the tubular body to increase the tear strength at the distal end portion of the tubular body.

The width of strip member 13 is not particularly limited, but is preferably set to be ½ or less the circumference of the tubular body. Two or more strip members 13 may be formed as needed.

Weld line 14 can be formed by using two-color extruder 15 having two cylinders 15a and 15b as shown in FIGS. 4 and 5. In extruder 15, buffer plate 18 projects from the inner surface of inner mold 19 near an outlet portion of die 17. Buffer plate 18 has a thickness (e.g., 1 mm or less) large enough to interrupt a resin flow from cylinder 15a for molding strip member 13 at an intermediate portion of its width. Therefore, the resin flow forming strip member 13 is divided when it passes buffer plate 18, and thereafter, the divided flows are joined again. As a result, weld line 14 can be formed in a final product.

Figure 3:
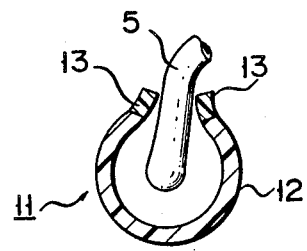
FIG. 3 is a sectional view showing the medical tool introduction cannula which is torn apart.

The position, height, and the like of buffer plate 18 can be appropriately determined in association with a blend of synthetic resins used. Normally, distance L between the distal end position of buffer plate 18 and the distal end of die 17 is set to be 0 to 5 mm, and a ratio of distance h between the upper end of buffer plate 18 and the inner wall of outer mold 20 to interval H of resin path 21 is set to be h:H=0 to ½:1 and preferably, 0 to 1/5:1. In this case, weld line 14 having a desired tear strength can be obtained. Since a coupling force at weld line 14 between two side portions is considerably smaller than that of the synthetic resin at the remaining circumferential portion, weld line 14 can be broken by applying an external stress, and can be easily torn, as shown in FIG. 3 to be separated from catheter 5.

The tear strength of weld line 14 can be adjusted by adjusting the position, height, width (length, thickness), and the like of buffer plate 18, or by adjusting types of resins or a blend of two or more resins constituting strip member 13.

One forming method of weld line 14 using the extruder in which buffer plate 18 projects from the inner mold, as shown in FIGS. 4 and 5, has been exemplified. However, the present invention is not limited to this, and other arbitrary molding means may be adopted. For example, as shown in FIGS. 6 and 7, the same buffer plate 18 as in FIGS. 4 and 5 may be provided to an outer mold of die 17 (the same reference numerals denote the same parts as in FIGS. 4 and 5). Although not shown, the same buffer plates may be provided to two or more portions of the outer or inner mold, or may be provided to both the outer and inner molds to oppose each other. In either case, the position (L), height (h), size, and the like of the buffer plate can be adjusted and selected in the same manner as in FIGS. 4 and 5.

A method of using the medical tool introduction cannula of the present invention will be described hereinafter.

Figure 8:
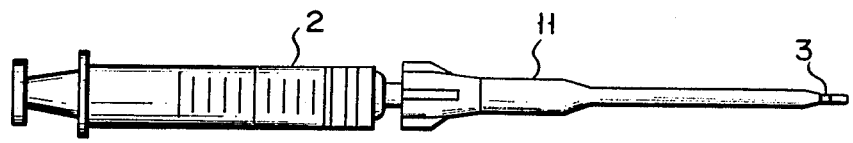
FIG. 8 to 10 are schematical view explaining the operation of the medical tool introduction cannula.
Figure 9:
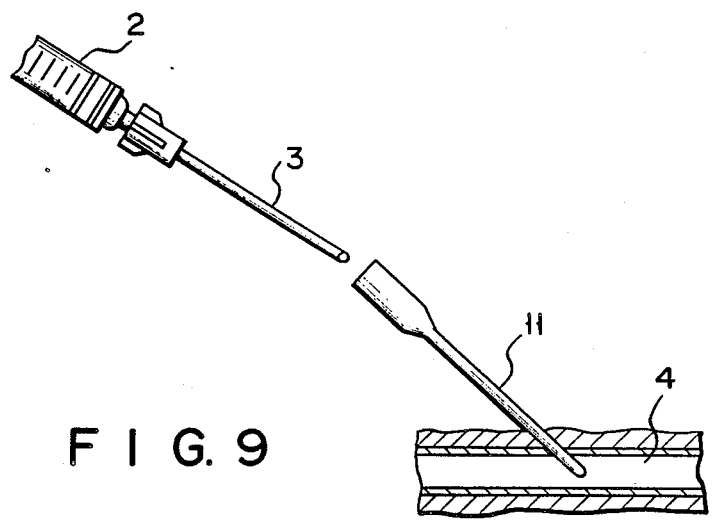
Figure 10:
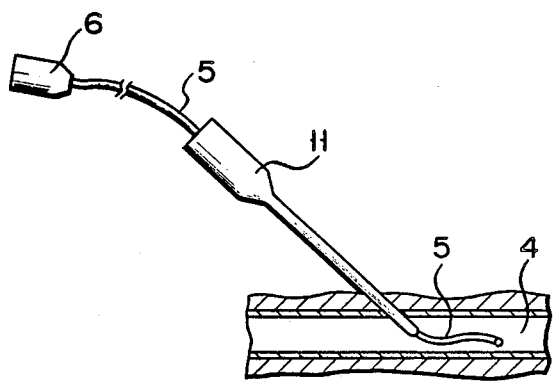

First, introduction cannula 11 is inserted in syringe 2 shown in FIG. 8, and is pierced into blood vessel 4 or the like together with inner cannula 3 of the syringe. Thereafter, as shown in FIG. 9, inner cannula 3 is pulled out to leave introduction cannula 11 in blood vessel 4. As shown in FIG. 10, catheter 5 is then inserted in introduction cannula 11, and is introduced into blood vessel 4.

When used introduction cannula 11 is removed from catheter 5, the proximal end portion of weld line 14 is cut by applying an external stress to introduction cannula 11, as shown in FIG. 3, and weld line 14 is then torn through the proximal end portion. Thus, introduction cannula 11 can be easily removed from catheter 5.

In this embodiment, a catheter is introduced using the medical tool introduction cannula. The present invention is not limited to the catheter but may be applied when various other rod-like medical tools are introduced in a human body.

A medical tool introduction cannula according to the second means of the present invention will be described with reference to an embodiment shown in FIGS. 11 to 16. FIG. 11 is a perspective view showing medical tool introduction cannula 31 according to the present invention. Introduction cannula 31 is constituted by first strip member portion 33 which consists of a mixture of first and second materials and is formed into a tubular shape except for strip member portion 32, and second strip member 34 which is formed along the longitudinal direction of medical tool introduction cannula 31 and consists of a third material, as shown in FIGS. 11 and 12. In introduction cannula 31, portions having different diameters are simultaneously formed by different-diameter extrusion.

Examples of the first material are polyolefin-based resins such as high-density polyethylene, polypropylene, an ethylene-propylene copolymer, and the like. The second material must be able to form a blend polymer with the first material, and have good bonding property with the third material (to be described later). That is, the second material must have a bonding property satisfying the following requirements. Upon introduction of the cannula to a human body, bonding surfaces of first and second strip members 33 and 34 are not separated, and smooth introduction can be assured without leakage of blood. Examples of the second material are materials prepared by modifying olefin-based resins such as high-density polyethylene, polypropylene, ethylene-propylene copolymer, and the like with maleic acid. The second material is preferably selected to contain the same type of base polymer as that of the first material. The third material must essentially have no bonding property with the first material. That is, the bonding property of the third material with the first material is weakened to allow separation of the bonding surfaces between first and second strip members 33 and 34 with a predetermined force. In addition, the third material must have good bonding property with the second material. Examples of the third material are polyamide resins such as 6-nylon, 6,6-nylon, 11-nylon, and the like or polyester-based resins such as polyethylene terephthalate, polybutylene terephthalate, and the like.

The first material may consist of a material selected from the group consisting of polypropylene, polyethylene, and ethylene-vinyl acetate, and the second and third materials may consist of a material selected from the group consisting of polypropylene, polyethylene, and ethylene-vinyl acetate, and having no compatibility with the first material.

As any of these materials, a synthetic resin is preferable in view of machinability. However, any material may be used if the above-mentioned requirements are satisfied.

In this manner, when first and second strip members 33 and 34 are combined, bonding and peeling properties between them depend on the type of the second material and a mixing ratio of the first and second materials. Therefore, the mixing ratio of the second material is appropriately adjusted in accordance with the shape and thickness of strip members 33 and 34, thereby freely adjusting the bonding and peeling properties between first and second strip members 33 and 34 to desired strengths.

When the first material employs a polyolefin-based resin, the second material employs a maleic acid-modified polyolefin resin, and the third material employs a polyamide or polyester resin, the mixing ratio of the first and second materials is adjusted to fall within the range of 10:1 to 2:1, and more preferably, 6:1 to 3:1.

When the first and second materials employ a blend polymer of an ethylene-vinyl acetate copolymer and polypropylene, and the third material employs polypropylene, the ratio of the ethylene-vinyl acetate copolymer:polypropylene is preferably adjusted to fall within the range of 1:1 to 1:5. At a mixing ratio falling within the range of 1:1 to 1:5, a product having good molding property and appropriate division property can be manufactured. More specifically, if the content of the ethylene-vinyl acetate copolymer is given as 1, when the content of polypropylene is less than 1, the mechanical strength of the splitting portion is decreased, and leakage of blood may occur upon introduction of the catheter. If the content of the ethylene-vinyl acetate copolymer is given as 1, when the content of polypropylene exceeds 5, the resultant product is not easily split, resulting in poor operability.

Medical tool introduction cannula 31 is manufactured by an extruder shown in, e.g., FIG. 15. More specifically, the extruder comprises first extrusion device 42 having annular die 41 at its distal end portion, and second extrusion device 44 which has nozzle 43 open to an intermediate portion midway along a melted resin flow path at the upstream side of die 41. First and second extrusion devices 42 and 44 are operated at the same time, so that a tube in which second strip member 34 is embedded in slit portion 32 of introduction cannula 31 shown in FIG. 12 can be extruded from die 41. The sectional shape of strip member 34 depends on the extrusion amount ratio of extrusion devices 42 and 44 and the sectional shape of the opening of nozzle 43, and can be arbitrarily selected as needed.

The number of second strip members 34 provided to introduction cannula 31 is not limited to one as in this embodiment. As shown in FIG. 16, two or more strip members 34 may be radially formed. The relationship between the widths of first and second strip members 33 and 34 is not limited to the illustrated one, but may be appropriately selected.

The medical tool introduction cannula according to the second means can be used in the same manner as in the method described with reference to FIGS. 8 and 9. That is, a catheter is inserted in introduction cannula 31, and is introduced into a blood vessel or the like.

When used introduction cannula 31 is removed from the catheter, second strip member 34 facing up is pinched, as shown in FIG. 13, and is pulled upward, as shown in FIG. 14, so that second strip member 34 can be peeled while opening slit 32 at one end of cannula 31. Then, introduction cannula 31 can be easily removed from catheter 35 through slit 32.

In the first or second means, as a coloring agent used for coloring of a strip member to be divided or peeled or coloring of a portion excluding the strip member, arbitrary dyes or pigments may be used unless they adversely affect a human body. The color of the coloring agent is not particularly limited, and may be appropriately selected to match the types of products.

EXAMPLE 1

A pair of buffer plates each having a length of 22 mm and a width of 0.5 mm were provided to an outer mold of a die of a two-color extruder to be in contact with the inner wall of an inner mold, so that their distal ends opposed a die outlet port at an interval of 0.5 mm (i.e., in FIG. 7, "L"=0.5 mm). Polypropylene (MA-6 (tradename); available from Mitsubishi Petrochemical Co., Ltd.) was flowed into cylinder 15b for forming the main portion of a tubular body, and a mixture of polypropylene (PP) and an ethylene-vinyl acetate copolymer (EVA) (V-401S (tradename); available from Mitsubishi Petrochemical Co., Ltd.) (mixing ratio, PP:EVA=λto 90:20 to 10) was flowed into cylinder 15a for forming a strip member. At the same time, a takeup speed of a molded product was changed in two steps, thereby obtaining a continuous body of a catheter introduction cannula which had central and base portions of different sizes and complied with a 16G inner cannula. The continuous body was cut into predetermined pieces, and the distal end of each piece was machined. In this case, no cracking of the distal end portions occurred. When the introduction cannula of this example was pierced into a mongrel's blood vessel together with an inner cannula, neither burr nor crack of the distal end portion were observed. In addition, when the introduction cannula was split upon removal, it could be easily split.

A catheter introduction cannula was molded following the same procedures as in this example except that SPN-3575 (a product of Dai Nihon Inc Kagaku Kogyo Co. Ltd. Japan) was mixed as a coloring agent in the PP/EVA mixture. As a result, a blue strip member could be obtained.

EXAMPLE 2

Polypropylene (MA-6) was used as a first material, and maleic acid-modified polypropylene (Modic, P-300F; available from Mitsubishi Petrochemical Co., Ltd.) was used as a second material. These materials were mixed at a ratio of 4:1 (weight ratio) to prepare a blend polymer. As a third material, 6-nylon was used. These materials were extruded using an extruder shown in FIG. 15, thereby obtaining an introduction cannula complying with a 16G inner cannula. When the distal end of the resultant introduction cannula was machined to be in contact with the 16G inner cannula, no cracking of the distal end portion occurred. When the introduction cannula was pierced into a mongrel's blood vessel together with the inner cannula, neither burr nor crack were observed. In addition, when the introduction cannula was split upon removal, it could be easily split.

COMPARATIVE EXAMPLE 1

Polypropylene (MA-6) was used as a polymer for a first strip member, and polyethylene was used as a polymer for a second strip member. Then, an introduction cannula complying with a 16G inner cannula was obtained by extrusion. When the cannula was cut into pieces and the distal end portion of each piece was machined to be in tight contact with the 16G inner cannula, no accidental splitting occurred. However, when it was attempted to tear the introduction cannula at a boundary, the attempt was unsuccessful.

COMPARATIVE EXAMPLE 2

High-density polyethylene was used as a polymer for a first strip member, and polyvinyl chloride was used as a polymer for a second strip member. An introduction cannula was obtained following the same procedures as in Example 2. However, the boundary of this cannula was easily peeled with a very small force of, e.g., cutting, and machining could not be performed.

EXAMPLE 3

Ethylene-vinyl acetate (V-401S) was used as a first material, and polypropylene (MA-6) was used as a second material. These materials were mixed at a ratio of PP:EVA=3:1 (weight ratio) to prepare a blend polymer. As a third material, polypropylene (MA-6) was used. These materials were extruded using an extruder shown in FIG. 15 to obtain an introduction cannula complying with a 16G inner cannula. When the distal end portion of the resultant cannula was machined to be in contact with the 16G inner cannula, no cracking of the distal end portion was observed. When the introduction cannula was pierced into a mongrel's blood vessel together with the inner cannula, neither burr nor crack of the distal end portion were observed. In addition, when the introduction cannula was split upon removal, it could be easily split.

What is claimed is:

1. A medical tool introduction cannula for introducing a rod-like medical tool such as a catheter into a living body, wherein said introduction cannula comprises:
    a tubular body having a longitudinal hollow portion for receiving said medical tool therethrough;
    a plurality of strip members in said tubular body, and which are liquid-tightly integrated to extend along a longitudinal direction of said tubular body;
    one of said strip members comprising a molded body of a mixture of ethylene-vinyl acetate copolymer and polypropylene mixed at a weight ratio of 1:1 to 1:5; and
    another of said strip members disposed adjacent to and extending along said one strip member, and comprising a molded body of polypropylene;
    said one strip member and said another strip member being bonded with a strength that allows said strip member to be separated from said another strip member by hand.

2. The medical tool introduction cannula of claim 1, wherein said weight ratio is within the range of 1:3 to 1:5.

3. The medical tool introduction cannula of claim 1, wherein said one strip member is made of a colored material.

4. The medical tool introduction cannula of claim 3, wherein said another strip member is made from a colored material.

5. The medical tool introduction cannula of claim 1, wherein said another strip member is made from a colored material.

6. The medical tool introduction cannula of claim 1, wherein said one strip member and said other strip member are made of colored materials having different colors.

7. A medical instrument assembly, comprising:
    an introduction cannula for introducing a rod-like medical tool such as a catheter into a living body, said introduction cannula comprising:
        a tubular body having a longitudinal hollow portion for receiving said medical tool therethrough;
        a plurality of strip members in said tubular body, and which are liquid-tightly integrated to extend along a longitudinal direction of said tubular body;
        one of said strip members comprising a molded body of a mixture of ethylene-vinyl acetate copolymer and polypropylene mixed at a weight ratio of 1:1 to 1:5;
        another of said strip members disposed adjacent to and extending along said one strip member, and comprising molded body of polypropylene; and
        said one strip member and said another strip member being bonded with a strength that allows said one strip member to be separated from said another strip member by hand; and
    a syringe having an inner cannula and detachably inserted into said medical tool introduction cannula such that a distal end of said inner cannula of said syringe projects from a tip end of said medical tool introduction cannula.

* * * * *